(12) United States Patent
Wilhoit (10) Patent No.: US 8,809,614 B2
(45) Date of Patent: Aug. 19, 2014

(54) DENTAL WOUND DRESSING

(76) Inventor: Jerry M. Wilhoit, Greeneville, TN (US)

( * ) Notice: Subject to any disclaimer, the term of this patent is extended or adjusted under 35 U.S.C. 154(b) by 173 days.

(21) Appl. No.: 13/351,055

(22) Filed: Jan. 16, 2012

(65) Prior Publication Data

US 2013/0183635 A1    Jul. 18, 2013

(51) Int. Cl.
*A61F 13/00* (2006.01)

(52) U.S. Cl.
USPC ............ 602/48; 602/46; 424/435; 424/443

(58) Field of Classification Search
CPC .......... A61C 7/00; A61C 7/12; A61C 7/20; A61C 7/36; A61C 7/125; A61C 7/002; A61C 7/146; A61C 5/122; A61C 9/0033; A61C 9/004; A61C 5/14; A61C 17/043; A61C 13/0004; A61C 19/06; A61C 19/063; A61F 2007/0261; A61F 2007/0285; A61F 2007/108
USPC ............ 602/48, 55–56; 433/6–7, 35–36, 31, 433/136, 22, 24, 116, 67–68; 607/96, 108, 607/112, 114; 424/435, 443, 445, 447, 485, 424/401, 52; 15/104.93, 167.1; 604/77; 514/163; 128/112.1
See application file for complete search history.

(56) References Cited

U.S. PATENT DOCUMENTS

| | | | |
|---|---|---|---|
| 3,175,558 A | 3/1965 | Caillouette et al. | |
| 3,545,230 A | 12/1970 | Morse | |
| 3,705,585 A * | 12/1972 | Saffro | 604/385.01 |
| 3,885,403 A | 5/1975 | Spencer | |
| 4,534,354 A | 8/1985 | Bonner, Jr. et al. | |
| 4,838,253 A | 6/1989 | Brassington et al. | |
| 5,160,328 A | 11/1992 | Cartmell et al. | |
| 5,188,103 A | 2/1993 | Smith | |
| 5,431,622 A | 7/1995 | Pyrozyk et al. | |
| 5,674,523 A | 10/1997 | Cartmell et al. | |
| 5,810,755 A | 9/1998 | LeVeen et al. | |
| 5,899,871 A | 5/1999 | Cartmell et al. | |
| 6,217,606 B1 * | 4/2001 | Portnoy et al. | 607/96 |
| 6,582,383 B2 | 6/2003 | Horning | |
| 6,599,262 B1 | 7/2003 | Masini | |
| 7,351,217 B2 | 4/2008 | Scherpenborg | |
| 7,402,721 B2 | 7/2008 | Sigurjonsson et al. | |
| 7,459,598 B2 | 12/2008 | Sigurjonsson et al. | |
| 7,897,832 B2 | 3/2011 | McAdams et al. | |
| 7,999,023 B2 | 8/2011 | Menon et al. | |
| 8,113,837 B2 * | 2/2012 | Zegarelli | 433/215 |
| 2004/0167456 A1 * | 8/2004 | Kingsford et al. | 602/48 |
| 2010/0234784 A1 | 9/2010 | Hartwell | |
| 2011/0143312 A1 * | 6/2011 | McAdams et al. | 433/138 |

* cited by examiner

*Primary Examiner* — Ophelia A Hawthorne
(74) *Attorney, Agent, or Firm* — Pitts & Lake, P.C.

(57) ABSTRACT

A dental dressing to promote healing and relieve pain and swelling associated with exposed dental alveoli. The dressing includes a three-dimensional dressing matrix to absorb leaked fluid associated with one or more exposed alveoli, and a therapeutic member to provide substantially localized cold therapy to one or more exposed alveoli, the therapeutic member embedded substantially within the dressing matrix and shaped to substantially engage one or more exposed alveoli while fitting substantially between contiguous teeth. At least part of the dressing matrix substantially conforms to one or more exposed alveoli, thereby engaging the therapeutic member with one or more exposed alveoli.

15 Claims, 8 Drawing Sheets

DENTAL WOUND DRESSING

CROSS-REFERENCE TO RELATED APPLICATIONS

Not Applicable

FIELD OF INVENTION

The present general inventive concept relates to a wound dressing for exposed dental alveoli that can be applied during or after a dental procedure or trauma to promote healing, relieve pain and swelling, and ameliorate bleeding.

BACKGROUND

Inside the human mouth, teeth are disposed in dental alveoli, commonly referred to as tooth sockets. Dental alveoli and teeth are included on both the maxilla (upper jaw) and mandible (lower jaw). Typically, twenty (20) primary or "baby" teeth are initially grown that eventually fall out and are replaced by twenty-eight (28) permanent or "adult" teeth. Some individuals experience the growth of up to four (4) third molars or "wisdom teeth" as well.

Various problems can manifest in teeth and tooth sockets. For instance, bacteria can be a frequent cause of tooth decay. Sometimes, the extent of such decay precipitates the extraction or removal of said tooth by a dentist, oral surgeon, or other medical practitioner. Tooth extraction can be achieved, for example, by grasping the tooth with forceps and performing a rocking motion to loosen the tooth from the alveolar bone. The tooth is loosened from the alveolar bone when connecting ligaments, or periodontal ligaments, that secure the tooth in place are gradually broken. Eventually, the tooth may be removed from the socket, thus exposing the dental alveolus.

Tooth extraction may also be required when, for instance, certain teeth are causing overcrowding in the mouth, malocclusion, or preventing the eruption of other teeth from the gum line. Wisdom teeth extraction has increased in popularity over the years. Further, tooth extraction frequently occurs prior to and in preparation for orthodontic treatment such as braces or dentures. Additionally, tooth extraction may also be precipitated by gum disease and/or cancer.

Trauma to the oral cavity and contained tissue and structures can also effectuate or require the removal of teeth. Occasionally, self induced trauma is caused by attempts at extracting primary teeth. More frequently, car accidents, sporting events, and the like cause trauma to the oral cavity and result in undesired tooth extraction.

Pain and bleeding are common during and after tooth extraction procedures and events. Pain is frequently caused by alveolitis, or swelling of the tooth socket, whereas bleeding results from the manipulation and/or destruction of proximate tissue. Alveolar osteitis, or dry sockets, can also materialize in the exposed tooth socket following tooth extraction when a blood clot forms, thereby depriving the tooth socket of blood. While the cause of this complication is substantially unknown, the associated pain is readily appreciated by anyone who has experienced dry sockets. In this regard, prevention is generally promoted by encouragement to keep the exposed socket clean and moist. Further, treatment is typically effectuated by applying medicated paste containing, for example, eugenol, benzocaine, and/or iodophorm. Hydrogel dressings, which release water to maintain a moist wound environment, have also been used in this context.

Methods of promoting healing, alleviating pain and swelling, and ameliorating bleeding are known in the art. Gauze pads, tulle, cottons swabs, or the like can be introduced into the oral cavity and compressed against the exposed alveolus to promote hemostasis and absorb blood and other leaked fluid. Pressure is particularly important for achieving hemostasis, however bioactive ingredients such as chitosan can serve as an effective supplement. For instance, U.S. Pat. No. 7,897,832 discloses dental dressing assemblies that are formed from hydrophilic polymer sponge structures, such as densified chitosan biomaterial.

Another known supplement that can be combined with pressure to assist in achieving hemostasis is tannin. Tannins are present in many woods, where they provide a partial defense against wildfires, decomposition, and infestation. Tannin is also a frequent ingredient in tea and is typically sold commercially as tannic acid. Tannin is known to constrict blood vessels in tissue and is a topical substance. Therefore, doctors frequently suggest biting down on a tea bag containing tannin following tooth extraction to help stop bleeding. Research also suggests that tannin has antiviral, antimicrobial, and antibacterial properties.

Hemostasis is also achieved, in part, by coagulation, or clotting, of the blood. Briefly, coagulation occurs when damaged blood vessels are covered by platelets and fibrin. Fifteen primary factors are required for blood to coagulate. Among those factors are fibrinogen and calcium. Both the intrinsic and extrinsic pathways associated with coagulation require ample amounts of calcium to initiate and progress the cascade of chemical reactions that cause coagulation. Chitosan is also known to help promote coagulation.

Figure 15A:
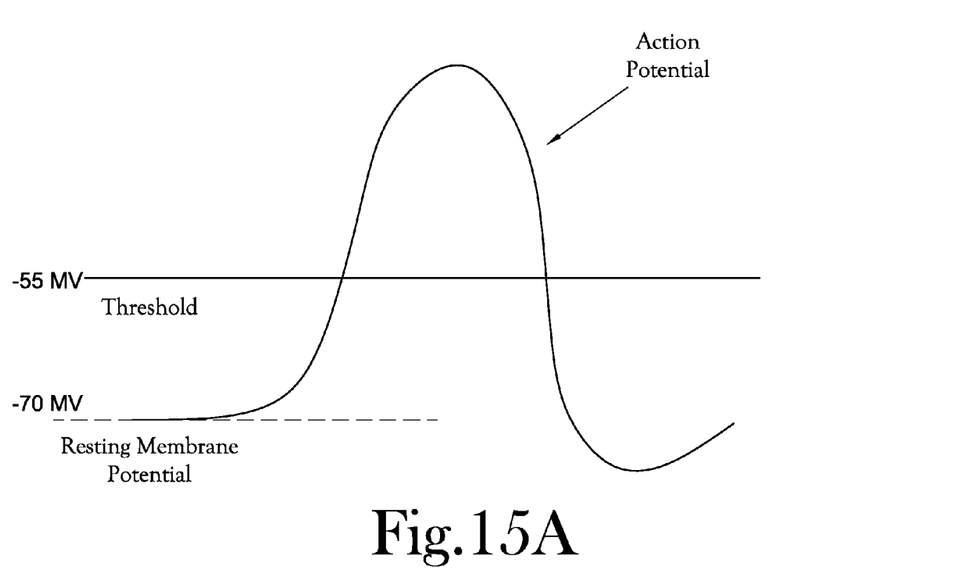
FIGS. 15A & 15B illustrate two example neuron membrane voltage sin curves, with FIG. 15A illustrating a normal neuron membrane with a resting membrane potential of −70 millivolts, and FIG. 15B illustrating a membrane with a resting membrane potential of −80 millivolts.
Figure 15B:
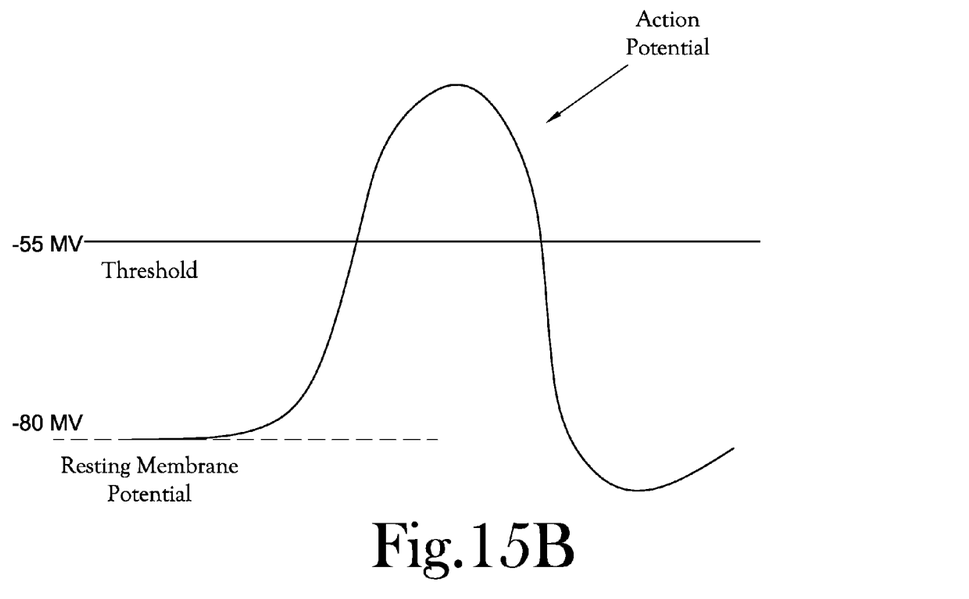

Pain and swelling associated with tooth extraction are often combated by applying cold therapy to the oral cavity. Typically, this is achieved by placing an ice pack or like device on the exterior of one's cheek, proximate the exposed tooth socket. Most individuals experience some pain relief when their wound site is exposed to cold therapy. Cold therapy is an effective pain remedy because cold temperature, when applied to nerve cells, lowers the resting membrane potential of the individual neurons. FIGS. 15A & 15B illustrate example sin curves of neurons responding to a stimulus. Neurons transmit electrical signals in response to stimuli by increasing the voltage within the membrane of a neuron to surpass a certain threshold level, also referred to as action potential. FIG. 15A illustrates an example voltage increase of a normal membrane having a resting potential of −70 millivolts. In order to achieve action potential for the electrical signal to be transmitted to the next neuron, the voltage increase from the resting membrane potential of −70 millivolts must surpass a certain threshold level of millivolts, in this instance −55 millivolts. Thus, when the resting membrane potential is lowered, for instance by cold therapy, as illustrated in FIG. 15B, a higher voltage increase will be necessary to achieve the threshold level required for transmission of the electrical signal. Therefore, lowering the resting membrane potential enough so as to preclude the voltage increase from surpassing the threshold level will prevent the sensation of pain to be transmitted between neurons.

Likewise, swelling often subsides when cold therapy is applied to the swollen tissue. Swelling is frequently caused by an excess amount of blood and fluid leaking from ruptured capillaries. Cold temperature causes the blood vessels within the swollen tissue to constrict or narrow. Also called vasoconstriction, this occurs when the smooth muscle within the blood vessels contract and clamp down, thereby minimizing and/or preventing further leakage of blood and serum. By this same principle, vasoconstriction also plays a critical role in achieving hemostasis.

Ice packs, however, frequently go too far in terms of applying cold therapy to the exterior of a cheek. Ice and other frozen things can create cold burns on the skin. Even more dangerous is when ice causes the skin to become numb, thus preventing the individual from noticing the tissue damage taking place. Further, cold therapy applied on the exterior of the cheek is not an efficient application of such therapy to an exposed tooth socket. Having to travel from the exterior of the cheek, through the skin and tissue, and then into an exposed tooth socket prevents the efficient application of cold therapy to the tooth socket. Additionally, the regional application of cold therapy minimizes the pain relief desired for the specific wound site. Stated differently, the lack of focused cold therapy applied locally to the tooth socket sacrifices the therapeutic effectiveness of the ice pack.

Thus, what is desired is a dental dressing capable of applying localized cold therapy to an exposed tooth socket without using ice or other frozen things. More particularly, what is needed is a dental dressing containing a pre-shaped therapeutic member that can fit in an exposed tooth socket, substantially between contiguous teeth, and apply localized cold therapy to the exposed socket while also helping prevent post-operative complications. Further desired is a dental dressing capable of containing moisture and topical agents that, when applied to an exposed tooth socket, promote healing and/or reduce pain.

BRIEF SUMMARY

The present general inventive concept provides a dental dressing to promote healing and relieve pain and swelling associated with exposed dental alveoli (tooth sockets). In some embodiments, the dental dressing includes a three-dimensional dressing matrix to absorb leaked fluid associated with one or more exposed alveoli, and a therapeutic member to provide substantially localized cold therapy to one or more exposed alveoli, with the therapeutic member embedded substantially within the dressing matrix and shaped to substantially engage one or more exposed alveoli while fitting substantially between contiguous teeth; whereby at least part of the dressing matrix substantially conforms to one or more exposed alveoli, thereby engaging the therapeutic member with the one or more exposed alveoli.

In some embodiments of the present general inventive concept, the dressing matrix is gauze, tulle, cotton, and/or any combination thereof. In other embodiments, the dressing matrix includes hydrogel, alginate, hydrofibre, chitosan, and/or any combination thereof.

In some embodiments, the therapeutic member is substantially made of gel substantially contained within a membrane. In some embodiments, the gel is substantially non-migrating. In other embodiments, the therapeutic member is substantially made of ammonium nitrate and water substantially contained within a polymer-based housing member. In yet other embodiments, the therapeutic member is substantially made of rubbing alcohol and water substantially contained within a polymer-based housing member.

In some embodiments of the present general inventive concept, the therapeutic member is substantially U-shaped so as to engage one or more exposed alveoli. In other embodiments, the therapeutic member includes a substantially U-shaped cross section, and is elongated to engage a plurality of adjacent, exposed alveoli. In other embodiments, the therapeutic member is substantially H-shaped so as to engage substantially aligned maxillary and mandibular exposed alveoli. In yet other embodiments, the therapeutic member includes a substantially H-shaped cross section and is elongated to engage a plurality of adjacent, substantially aligned, exposed maxillary and mandibular alveoli. Still, in other embodiments, the therapeutic member includes a socket cover portion and at least two tapered arm members angularly extending from the cover portion.

In some embodiments, the dental dressing further includes a moisture-releasing insert, with the insert embedded substantially within the dressing matrix, substantially adjacent to the therapeutic member. In some embodiments, the moisture-releasing insert includes hydrogel, hydrocolloid, hydrofibre, and/or any combination thereof. In some embodiments, the dental dressing includes a topical agent insert, with the insert embedded substantially within the dressing matrix, substantially adjacent to the therapeutic member. In some embodiments, the topical agent insert includes tannin. In other embodiments, the topical agent insert includes eugenol, benzocaine, iodophorm, soluble aspirin, zinc oxide, and/or any combination thereof.

Additional aspects and advantages of the present general inventive concept will be set forth in part in the description which follows, and, in part, will be obvious from the description, or may be learned by practice of the present general inventive concept.

BRIEF DESCRIPTION OF THE FIGURES

The following example embodiments are representative of example techniques and structures designed to carry out the objects of the present general inventive concept, but the present general inventive concept is not limited to these example embodiments. In the accompanying drawings and illustrations, the sizes and relative sizes, shapes, and qualities of lines, entities, and regions may be exaggerated for clarity. A wide variety of additional embodiments will be more readily understood and appreciated through the following detailed description of the example embodiments, with reference to the accompanying drawings in which.

DETAILED DESCRIPTION

Reference will now be made to various example embodiments of the present general inventive concept, examples of which are illustrated in the accompanying drawings and illustrations. The example embodiments are described herein in order to explain the present general inventive concept by referring to the figures. The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art.

Figure 1:
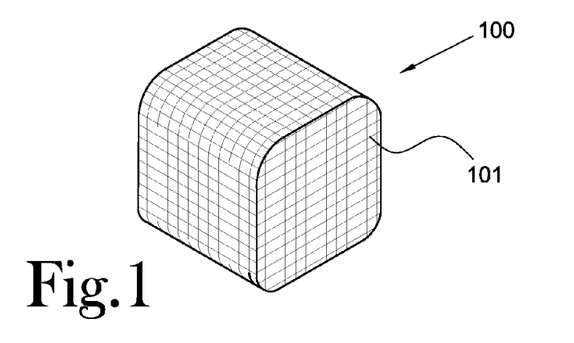
FIG. 1 illustrates a perspective view of an example embodiment of the present general inventive concept, showing the exterior of the dressing matrix.
Figures 2, 3A, 3B:
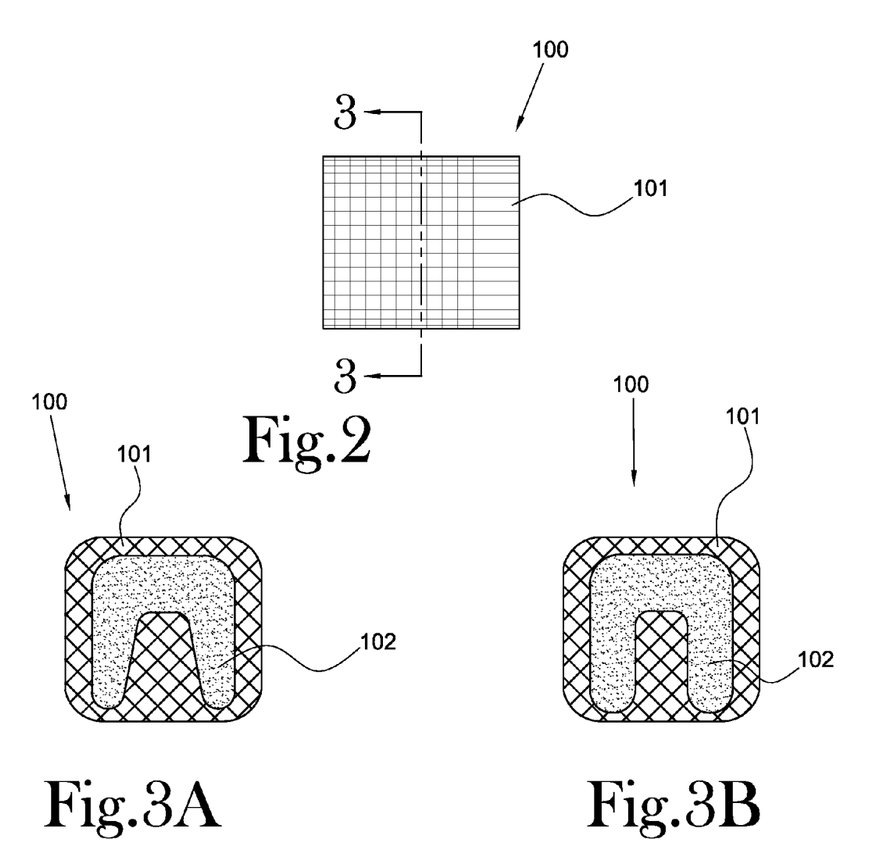
FIG. 2 illustrates a side view of the embodiment shown by FIG. 1.
FIGS. 3A & 3B illustrate cross-sectional views of the embodiment shown in FIG. 2, with FIG. 3A portraying an example embodiment of the present inventive concept and FIG. 3B portraying another example embodiment of the present inventive concept.

A dental wound dressing 100 for exposed dental alveoli, or tooth sockets, in accordance with various embodiments of the present general inventive concept, is shown generally in FIGS. 1-3B. FIG. 1 illustrates an exterior, perspective view of an example embodiment of the present general inventive concept. FIG. 2 illustrates the same embodiment from FIG. 1, only from a side view with a cross-sectional cutting line 3, designating the cross sectional views of example embodiments of the present general inventive concept illustrated by FIGS. 3A & 3B.

A dental dressing 100 for exposed tooth sockets includes an exterior dressing matrix 101. The dressing matrix 101 can be a three-dimensional mass of dressing material that adapts to various spatial requirements. For instance, one suitable dressing matrix 101 is gauze. Gauze can be shaped, configured, and manipulated to conform to a given space. Moreover, gauze is adaptable to the particular morphology and topology concerns of an exposed tooth socket. Also important, gauze provides an appropriate medium to absorb blood and other leaked fluids from the wound site. One skilled in the art will understand that the present general inventive concept is not limited to using gauze. For instance, cotton swabs, tulle, and the like, or any combination thereof, can also be used. Further, dressings containing topical agents and bio-ingredients such as, for example, hydrogel, alginate, hydrofibre, collagen, chitosan, or any combination thereof, can also work. Other suitable dressing matrices will be apparent to those skilled in the art, and may be used without deviating from the scope or spirit of the present general inventive concept.

Embedded substantially within the dressing matrix 101, is a therapeutic member 102. In the illustrated embodiment, the therapeutic member 102 is substantially comprised of gel contained within a membrane. More specifically, in the illustrated embodiment, the therapeutic member 102 is substantially comprised of substantially non-migrating gel. Stated differently, the gel in the present embodiment is substantially rigid and effective at substantially retaining its shape under pressure. One suitable gel is manufactured and sold by King Brand Health Care Products Limited under the trade name RigiGel®. One skilled in the art, however, will recognize that other substantially rigid and substantially non-migrating gels can be substituted without deviating from the scope or spirit of the general present inventive concept.

Further, in some embodiments of the general present inventive concept, the gel can also be temperature sensitive. Stated differently, the gel can substantially retain its temperature after introduction into hot or cold environments and subsequent removal therefrom. For instance, the gel can be placed in a refrigerator or freezer for a selected duration. Upon removal from the cold environment, the gel will substantially retain its cold temperature. One suitable gel is manufactured and sold by King Brand Health Care Products Limited under the trade name RigiGel®. One skilled in the art will recognize that other temperature sensitive gels can be used without deviating from the scope or spirit of the general present inventive concept.

One skilled in the art will understand that the present general inventive concept is not limited to a therapeutic member 102 that is comprised of gel. On the contrary, other substances with similar properties can comprise the therapeutic member 102. For instance, ammonium nitrate and water contained within a common housing member can combine to produce an endothermic reaction resulting in a cold product. Similarly, water and rubbing alcohol can also be mixed and stored in a cold environment. Of course, in order to create a therapeutic member 102, the above-mentioned ingredients will have to be contained in an exterior housing member that can be safely inserted into an oral cavity and engage an exposed tooth socket, while also substantially fitting between contiguous teeth. Further, in some embodiments, the exterior housing member can be relatively soft, so as to prevent damage to teeth applying pressure to the dental dressing 100. One skilled in the art will recognize that several polymer-based materials can be used to form an exterior housing member that is safe for insertion into an oral cavity. One skilled in the art will also understand, however, that the present general inventive concept is not limited to the above-mentioned substances. Other substances capable of retaining a cold temperature and being contained within a housing member can also be used without departing from the scope or spirit of the present general inventive concept.

FIG. 3A illustrates a cross-sectional view of an example embodiment of the present general inventive concept with the therapeutic member 102 in the general shape of a "U," but having tapered and angled side arms. Stated differently, the embodiment illustrated in FIG. 3A includes a cover portion to cover an exposed tooth socket (i.e., socket cover portion), and two tapered arm members angularly extending from opposing sides of the socket cover portion. FIG. 3B illustrates a cross-sectional view of another example embodiment of the present general inventive concept with the therapeutic member 102 in the general shape of a "U" without tapered or angled arm members. Stated differently, the embodiment in FIG. 3B includes a socket cover portion and two non-tapered arm members perpendicularly extending from the cover portion.

When engaging an exposed tooth socket, the therapeutic member 102 can be oriented such that it substantially covers and surrounds the exposed tooth socket while also fitting between contiguous teeth. Specifically, when engaging an exposed tooth socket, the cover portions of the present example embodiments can sit on top of, or be disposed directly underneath, one or more exposed tooth sockets, while the two tapered arm members laterally flank the one or more exposed tooth sockets on opposing sides of the oral epithelium. Stated differently, the therapeutic member 102 can superpose the exposed tooth socket as well as engage both sides of the oral epithelium and gingival tissue proximate the exposed socket, with one arm member engaging the facial surface of the proximate gum tissue, and the other arm member engaging the lingual surface of the proximate gum tissue.

The difference between the embodiment illustrated in FIG. 3A and the one illustrated in FIG. 3B is shape. The angled and flared arm members of the therapeutic member in FIG. 3A can provide a better fit for individuals with larger gums. Depending on the rigidity of the gel or housing comprising the therapeutic member 102 in the illustrated embodiment, the shape of the therapeutic member 102 can remain substantially the same even with force applied from the opposite jaw. Stated differently, in some embodiments the gel or housing of the therapeutic member 102 can be substantially rigid so as to substantially prevent significant flexing in the shape of the therapeutic member 102. Thus, for individuals with larger gums, the angled and tapered arm members can facilitate a better fit, while still permitting the therapeutic member to remain substantially between contiguous teeth. Further, the tapered arm members can also permit the inclusion of more dressing matrix 101. Stated differently, tapered arm members can occupy less volume than the non-tapered arm members of FIG. 3B, and therefore permit the dressing matrix 101 to occupy the excess volume that would be occupied by the non-tapered arm members. Providing more dressing matrix 101 to the dental dressing 100 will allow the dental dressing 100 to absorb more leaked fluid from the wound site.

Figure 4:
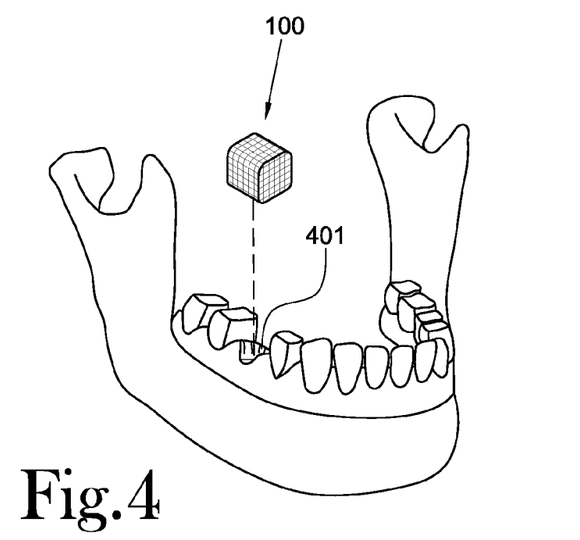
FIG. 4 illustrates an exploded view of an example embodiment of the present inventive concept engaging an exposed tooth socket.
Figure 5:
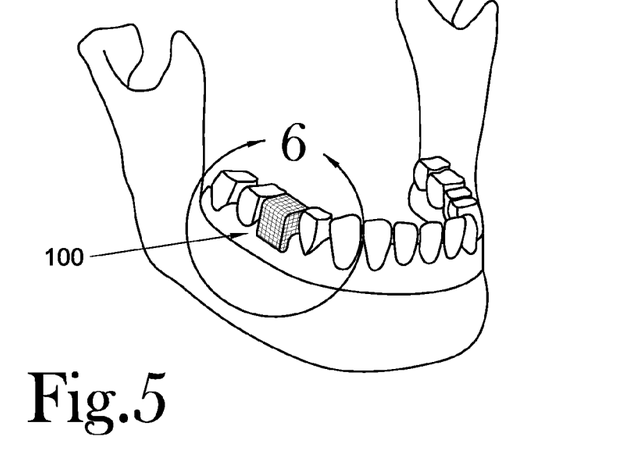
FIG. 5 illustrates the embodiment shown in FIG. 4 fully engaging an exposed tooth socket.
Figure 6:
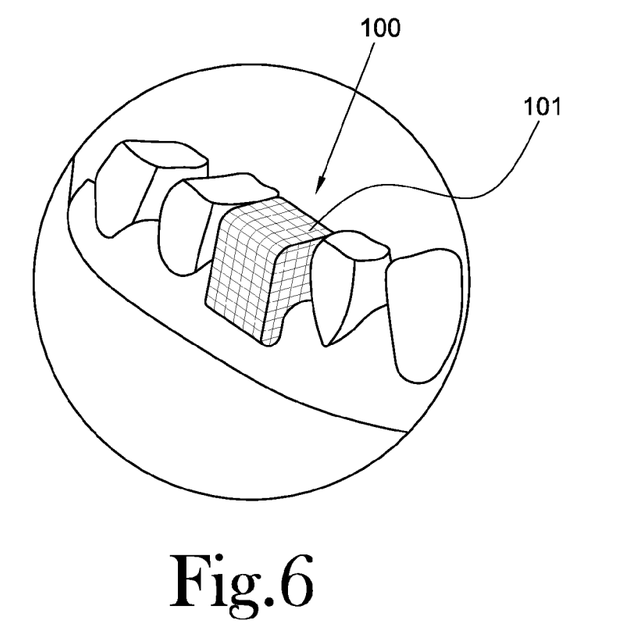
FIG. 6 illustrates a more detailed view of the example embodiment portrayed in FIG. 5.
Figure 7:
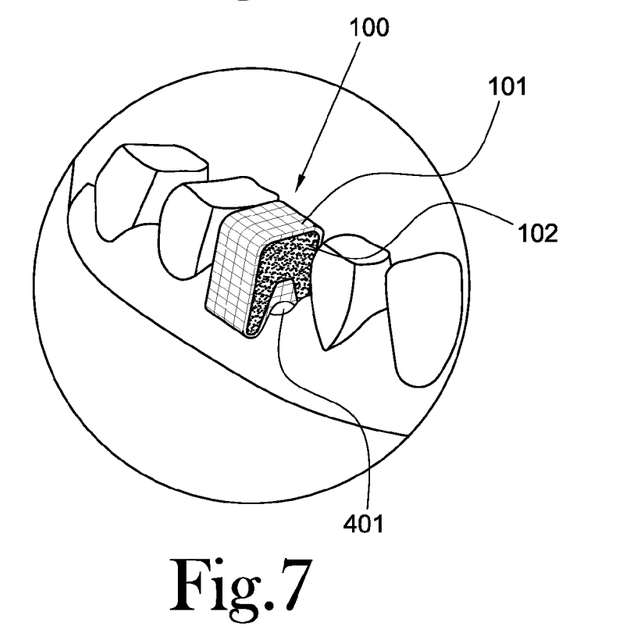
FIG. 7 illustrates a cross-sectional view of the example embodiment of FIG. 6.

FIGS. 4-7 illustrate an example embodiment of the present general inventive concept engaging an exposed tooth socket. FIG. 4 illustrates an exploded view of an example dental dressing 100 engaging an exposed tooth socket 401. FIGS. 5-7 illustrate an example dental dressing 100 fully engaged with an exposed tooth socket 401. Specifically, FIG. 6 illustrates a more detailed view of the embodiment portrayed in FIG. 5, and FIG. 7 illustrates a cross-sectional view of the embodiment portrayed in FIG. 6.

Each exposed tooth socket 401 contains particular morphological and topological concerns. For instance, an exposed tooth socket 401 generally contains a cavity, into which the root of a tooth is disposed and secured to the alveolar (jaw) bone with periodontal ligaments. Further, the gingival tissue immediately adjacent to and surrounding the cavity has specific contours and shapes. For example, the marginal and attached gingiva contain depressions, indentations, and grooves. In this regard, the dressing matrix 101 can substantially conform to the morphology and topology of the exposed tooth socket 401 and proximate gingival and epithelial tissue, and can be compressed to apply appropriate pressure for promoting hemostasis. The dressing matrix 101 can also be compressed such that part of it actually enters the cavity in the open socket 401. The pressure applied by the dressing matrix 101 substantially assists the wound site in achieving hemostasis.

Additionally, the dressing matrix 101 can be compressed against and into the exposed tooth socket 401 to fully engage the therapeutic member 102 with the exposed tooth socket 401. The therapeutic member 102 substantially covers and surrounds the exposed tooth socket and proximate tissue to relieve pain and reduce swelling, while fitting substantially between contiguous teeth. The therapeutic effectiveness of the therapeutic member 102 is significantly influenced by its proximity to the exposed tooth socket and proximate tissue. The proximity of the therapeutic member 102 to the exposed tooth socket is directly controlled by the amount and degree of compression of the dressing matrix 101 between the therapeutic member 102 and the exposed socket.

Referring specifically to FIGS. 6 & 7, the dressing matrix 101 has conformed to the exposed tooth socket 401. These figures illustrates how the dressing matrix 101 can compress against and into an exposed tooth socket 401 to achieve substantial proximity between the therapeutic member 102 and the exposed tooth socket 401 and proximate tissue. Accordingly, in the embodiments where the therapeutic member 102 is temperature sensitive, cold therapy can be applied to the exposed tooth socket 401 and proximate tissue by virtue of the proximity of the therapeutic member 102. The dressing matrix 101 absorbs any released fluids from the wound, such as blood, and provides pressure to the socket and proximate tissue to promote hemostasis. Further, as portrayed in the embodiment illustrated in FIG. 7, the side arms of the therapeutic member 102 can extend beyond the tooth line to engage both sides of the gingival tissue and oral epithelium proximate the exposed tooth socket 401. Stated differently, the side arms of the therapeutic member 102 can extend down below the tooth line and flank both sides of the exposed tooth socket to engage proximate gum tissue, thereby applying therapy to the blood vessels in the gum tissue below the extraction site. This helps relieve pain and decrease swelling associated with the exposed tooth socket.

Figure 8A:
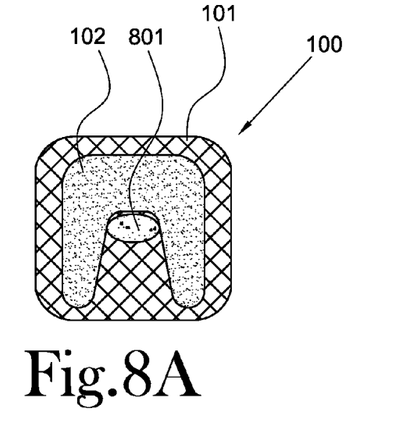
FIGS. 8A & 8B illustrate cross-sectional views of two example embodiments of the present inventive concept, both with a therapeutic member and a moisture-releasing insert embedded substantially within a dressing matrix.
Figure 8B:
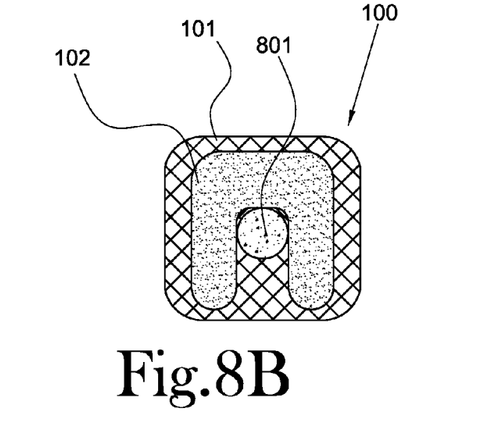
Figure 9A:
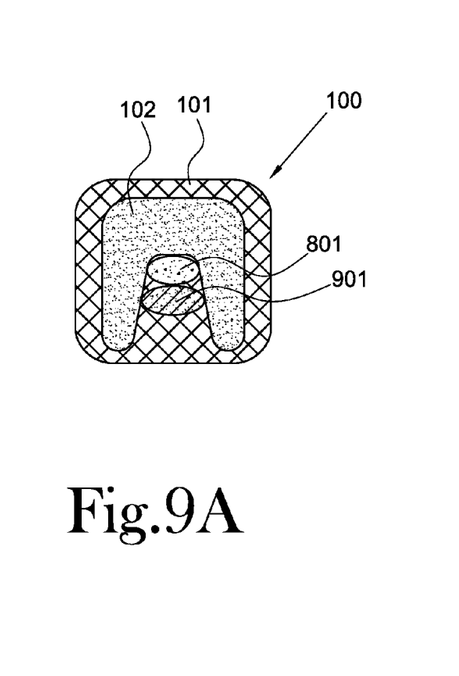
FIGS. 9A & 9B illustrate cross-sectional views of two example embodiments of the present inventive concept, both with a therapeutic member, a moisture-releasing insert, and a topical agent insert embedded substantially within a dressing matrix.
Figure 9B:
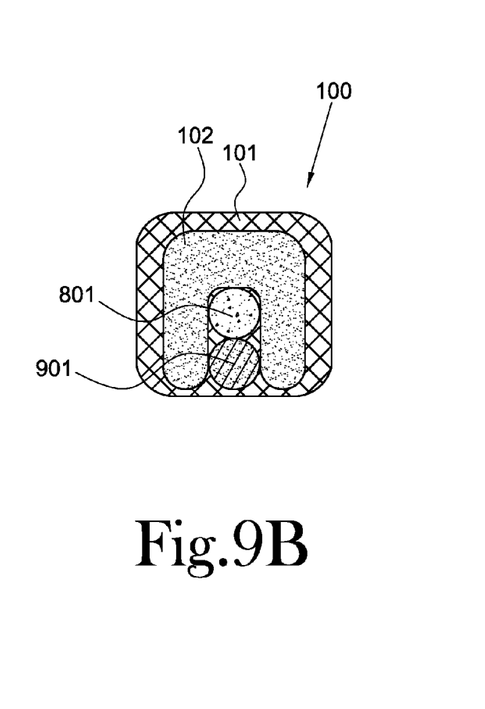

FIGS. 8-9B illustrate example embodiments of the therapeutic member 102, in accordance with various embodiments of the present general inventive concept. Specifically, FIG. 8A illustrates an example embodiment with the therapeutic member 102 having tapered and angled side arms. A moisture-releasing insert 801 is also included, embedded substantially within the dressing matrix 101. FIG. 8B illustrates an example embodiment with the therapeutic member having side arms disposed substantially perpendicularly from the socket cover portion. FIG. 8B also includes a moisture-releasing insert 801 embedded substantially within the dressing matrix 101. FIGS. 9A & 9B illustrate both example embodiment therapeutic members 102 discussed above, but also include a topical agent insert 901 also embedded substantially within the dressing matrix 101.

In the embodiments illustrated in FIGS. 8A & 8B, moisture-releasing inserts 801 are embedded substantially within the dressing matrices 101, substantially adjacent to the therapeutic member 102. In the illustrated embodiments, the moisture-releasing insert 801 is comprised of hydrogel. It will be understood that hydrogel is comprised of a network of hydrophilic polymer chains. The hydrogel inserts 801 in the illustrated embodiments release moisture to the exposed tooth socket and proximate tissue. Some have speculated that keeping the exposed sockets moist and clean may help prevent alveolar osteitis, or dry sockets. Although the oral cavity is substantially moist already, the dressing matrix 101 can have a tendency to cause dryness by soaking up all the proximate fluid, thereby depriving the wound site and proximate tissue of moisture. Including a hydrogel insert 801 can ensure that the exposed tooth socket remains moist. Similarly, other moisture-releasing inserts 801 containing hydrocolloids, hydrofibres, and/or any combination thereof can also be used to achieve similar results without departing from the scope or spirit of the present general inventive concept.

In the embodiments illustrated in FIGS. 9A & 9B, a topical agent insert 901 is included. The topical agent inserts 901 can be comprised of a number of different substances that can be topically applied to the wound site to promote healing and/or relieve pain and swelling. For example, tannin can be included in the insert 901 to promote vasoconstriction and prevent infection. A tea bag itself containing tannin is one suitable topical agent insert 901. In some embodiments, medications like eugenol (or oil of cloves extract), benzocaine, iodophorm, soluble aspirin, zinc oxide, or any combination thereof, can be included in the topical agent insert 901. Topical agent inserts 901 containing analgesics, such as eugenol, can be particularly effective immediately following tooth extraction when pain is almost always prevalent. However, analgesics and other medications are also effective in instances when dry sockets form after tooth extraction. One skilled in the art will recognize that other topical substances can be included without departing from the scope or spirit of the present general inventive concept.

In the illustrated embodiments, the moisture-releasing inserts 801 are disposed between the topical agent inserts 901 and the therapeutic members 102, all embedded substantially within the dressing matrix 101. Most topical agents envisioned to be included in the inserts 901 are water soluble. Therefore, disposing the moisture-releasing insert 801 between the topical agent and the therapeutic member 102 will ensure that the topical agent insert 901 becomes moist, thereby facilitating topical application to the exposed tooth socket 401. Moreover, the therapeutic effectiveness of the topical agent insert 901 is maximized by disposing it proximate to the wound site. However, one skilled in the art will understand that the relative disposition of the moisture-releasing inserts 801 and the topical agent inserts 901 described herein is non-limiting.

Figure 10A:
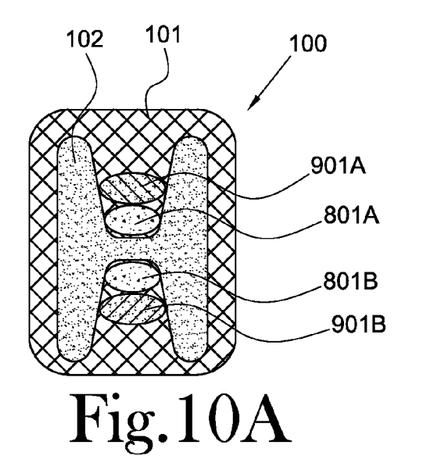
FIGS. 10A & 10B illustrate cross-sectional views of two example embodiments of the present inventive concept that can be applied to substantially aligned maxillary and mandibular exposed tooth sockets, both with a therapeutic member, a moisture-releasing insert, and a topical agent insert embedded substantially within a dressing matrix.
Figure 10B:
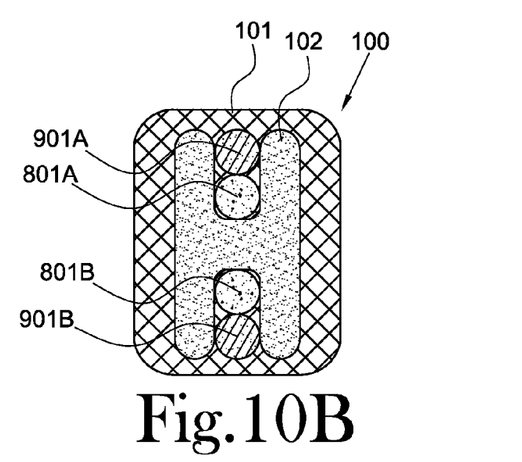

In the embodiments illustrated in FIGS. 10A-10D, the therapeutic members 102 are shaped, generally, as an "H." FIG. 10A illustrates an example embodiment therapeutic member 102 with tapered and angled side arms, whereas FIG. 10B illustrates another example embodiment therapeutic member 102 with non-tapered, substantially perpendicular arm members. Both of the example embodiments illustrated in FIGS. 10A & 10B include hydrogel inserts 801A & 801B and topical agent inserts 901A & 901B. These embodiments accommodate substantially aligned, maxillary and mandibular exposed tooth sockets. Stated differently, the present embodiments can provide therapy following an extraction of substantially aligned mandibular and maxillary teeth. For instance, oral, hockey injuries frequently effectuate or require extraction of substantially aligned maxillary and mandibular teeth. The present embodiments provide a therapeutic solution for those injuries contained within a single wound dressing 100.

Figure 10C:
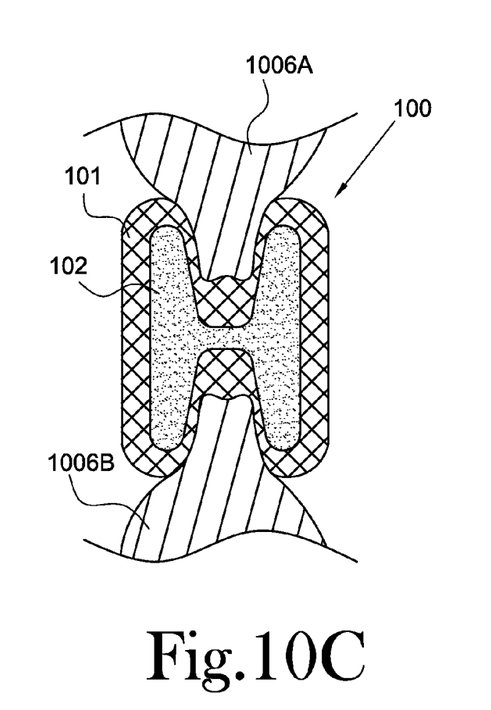
FIGS. 10C & 10D illustrate cross-sectional views of two example embodiments of the present inventive concept engaging substantially aligned, mandibular and maxillary exposed tooth sockets, with FIG. 10C including a therapeutic member embedded substantially within a dressing matrix, and FIG. 10D including a therapeutic member, a moisture-releasing insert, and a topical agent insert embedded substantially within a dressing matrix.
Figure 10D:
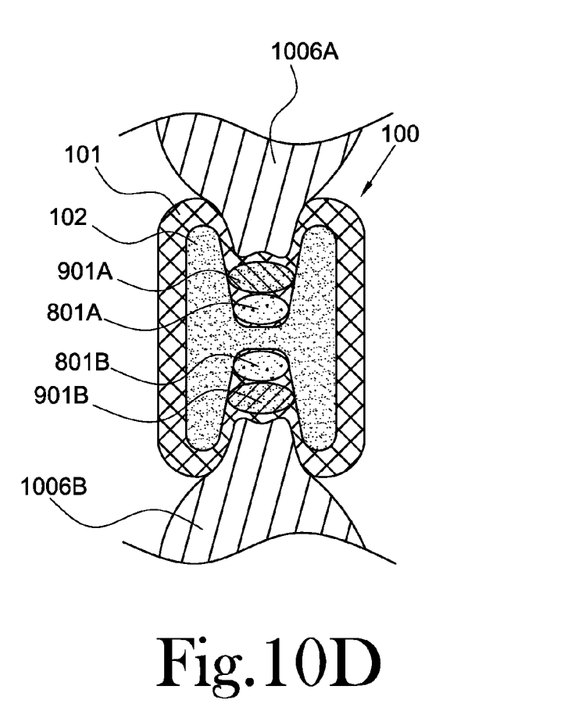

FIGS. 10C & 10D portray cross-sectional views of example embodiment, "H-shaped" dental wound dressings 100 engaging substantially aligned maxillary and mandibular exposed tooth sockets. The example embodiment illustrated in FIG. 10C includes only a therapeutic member 102 embedded substantially within a dressing matrix 101, whereas the example embodiment in FIG. 10D includes a therapeutic member 102, hydrogel inserts 801A & 801B, and topical agent inserts 901A & 901B embedded substantially within a dressing matrix 101. Proximate gum tissue is indicated at 1006A & 1006B. As shown, the side arms of the therapeutic member 102 flank the lingual and facial surfaces of the proximate gum tissue 1006A & 1006B to apply therapy to the blood vessels contained therein.

Figure 11:
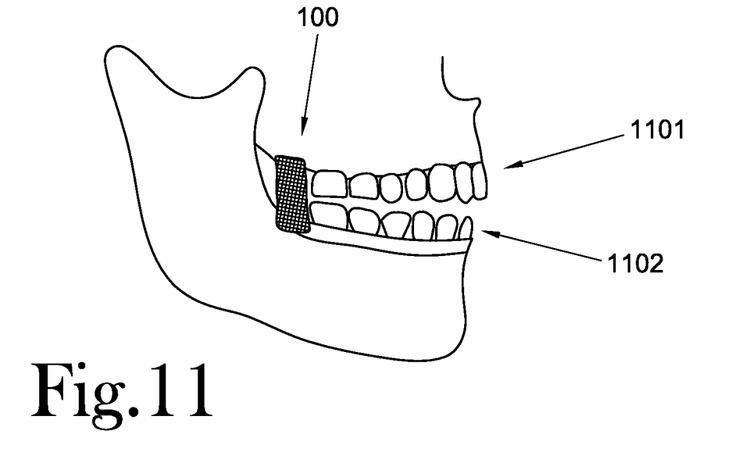
FIG. 11 illustrates an example embodiment of the present inventive concept engaging substantially aligned maxillary and mandibular exposed wisdom tooth sockets.

FIGS. 11-14 illustrate example embodiment dental wound dressings 100 that engage a plurality of exposed tooth sockets. For instance, FIG. 11 illustrates an example embodiment wound dressing 100 engaging substantially aligned maxillary 1101 and mandibular 1102 tooth sockets. Specifically, the dental dressing 100 in the illustrated embodiment is engaging substantially aligned and exposed third molar, or wisdom tooth, sockets. This embodiment accommodates the "H-shaped" example embodiment therapeutic members 102 illustrated in FIGS. 10A & 10B. The presently illustrated embodiment is installed inside a user's oral cavity by placing the dressing 100 in the desired location while the oral cavity is fully extended or open. The user will then close its oral cavity to the extent permitted by the dressing 100 to compress the dressing matrix 101 against the exposed tooth sockets and proximate tissue, thereby substantially engaging the therapeutic member 102 with the exposed sockets and proximate tissue.

Figure 12:
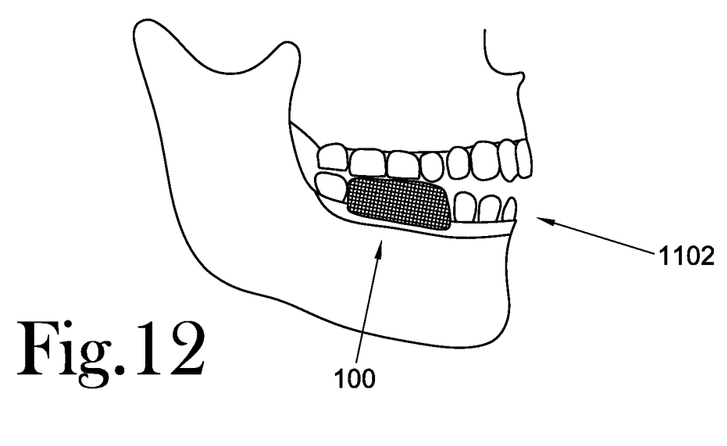
FIG. 12 illustrates an example embodiment of the present inventive concept engaging adjacent, exposed mandibular tooth sockets.
Figure 13:
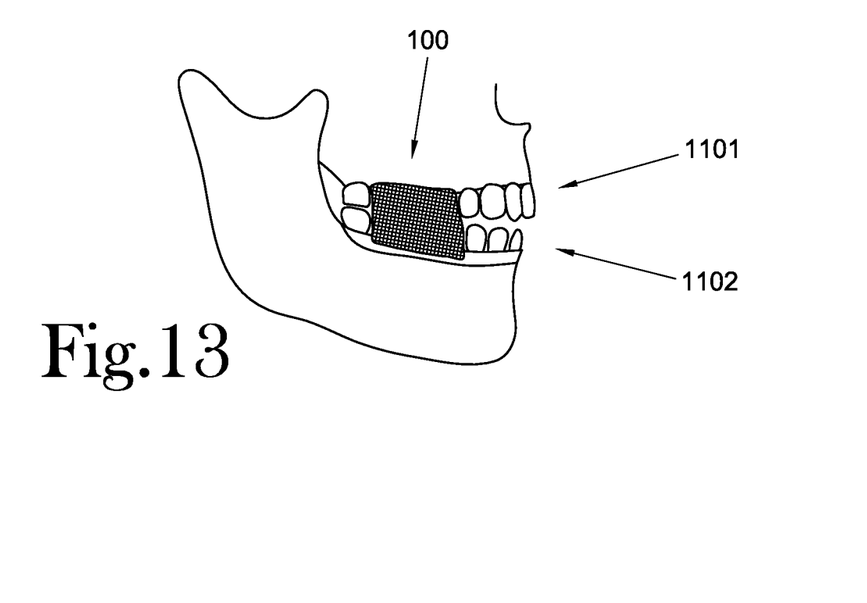
FIG. 13 illustrates an example embodiment of the present inventive concept engaging a plurality of adjacent, substantially aligned, maxillary and mandibular exposed tooth sockets.

FIG. 12 illustrates an example embodiment wound dressing 100 engaging a plurality of adjacent mandibular 1102 tooth sockets. The illustrated embodiment's therapeutic member 102 contains the same, substantially "U" shaped cross sections portrayed in FIGS. 3A & 3B, but is elongated to cover a plurality of adjacent, exposed tooth sockets. Like the embodiment illustrated in FIG. 11, installation into a user's oral cavity can be achieved by opening the oral cavity, inserting the dressing 100 into the selected location, and gently closing the oral cavity to compress the dressing matrix against and into the exposed sockets. FIG. 13 illustrates an example embodiment wound dressing 100 simultaneously engaging a plurality of adjacent, substantially aligned, maxillary 1101 and mandibular 1102 exposed tooth sockets. In the present embodiment, the therapeutic member 102 contains an "H-shaped" cross section portrayed in either FIG. 10A or FIG. 10B, but is elongated to accommodate a plurality of adjacent tooth sockets.

Figure 14:
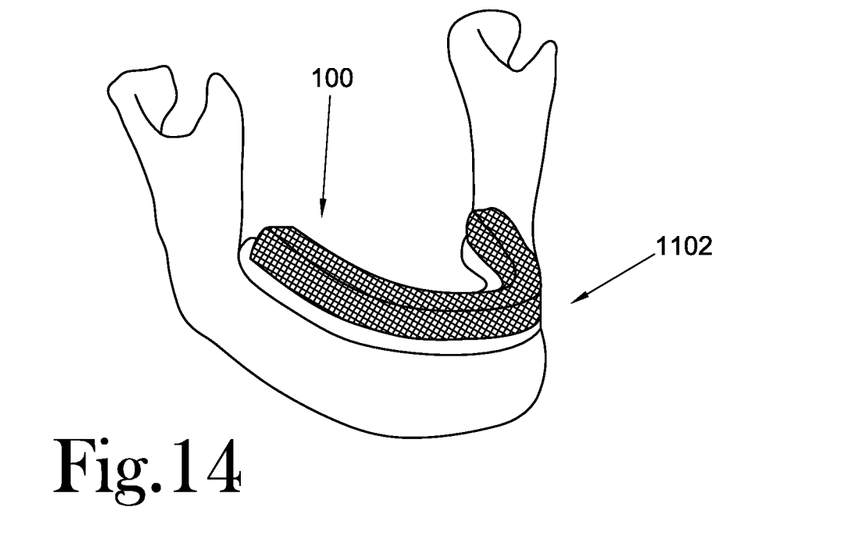
FIG. 14 illustrates an example embodiment of the present general inventive concept engaging an entire mandibular row of exposed tooth sockets.

FIG. 14 illustrates an example embodiment dental wound dressing 100 engaging an entire row of exposed, mandibular 1102 tooth sockets. In this regard, the presently illustrated embodiment resembles a conventional mouthpiece. The presently illustrated embodiment can be used following the extraction of an entire row of teeth, frequently in preparation for installing dentures. One skilled in the art will recognize that the present embodiment can also engage a row of exposed, maxillary 1101 tooth sockets. Thus, the present embodiment provides a therapeutic solution for the pain associated with a full row tooth extraction in a single dressing 100.

In some instances, an individual has both rows of teeth extracted. Stated differently, it is possible to have both maxillary 1101 and mandibular 1102 full row extractions occur at substantially the same time. Therefore, in some embodiments of the present general inventive concept, two dental dressings 100 bearing "U-shaped" cross-sections can each independently engage the maxillary row 1101 and mandibular row 1102. In this embodiment, because two dental dressings 100 are being used, a straw or other device can be inserted into the oral cavity between the two dental dressings 100. On the other hand, in other embodiments, one dental dressing bearing an "H-shaped" cross section can engage both the maxillary and mandibular row of exposed tooth sockets. However, in this embodiment, a straw or like device will not be able to be inserted into the user's oral cavity because of the single dental dressing engaging both the upper and lower rows of tooth sockets.

The embodiments described herein provide a dental dressing 100 for an exposed tooth socket including a therapeutic member 102 embedded substantially within a dressing matrix 101. The dressing matrix 101 can be adaptable to conform to various shapes and contours as required by the particular tooth socket. The therapeutic member 102 can be shaped to engage an exposed tooth socket and flank opposing sides of the oral epithelium, while fitting substantially between contiguous teeth. In some embodiments, the therapeutic member 102 is substantially comprised of rigid, substantially non-migrating gel contained within a membrane. In other embodiments, the therapeutic member is comprised of water and rubbing alcohol substantially contained within a polymer-based housing member. Following a tooth extraction, individuals can place the dental dressing 100 in a cold environment so that the therapeutic member becomes cold. Subsequently, the user can remove the dental dressing 100 from the cold environment and insert it into their oral cavity. The dressing matrix 101 can be compressed into the exposed socket, thereby engaging the embedded therapeutic member 102 with the exposed tooth socket. The dressing matrix 101, and the applied pressure, will help absorb leaked fluids and promote vasoconstriction, while the cold therapeutic member 102 will reduce swelling, promote vasoconstriction, and relieve pain.

In other embodiments, the therapeutic member 102 is comprised of ammonium nitrate and water substantially contained within a polymer-based housing member. Users can cause the therapeutic member 102 to become cold by effectuating an endothermic reaction with the ammonium nitrate and water, by, for example, shaking the therapeutic member 102 or inserting water into a housing member that already contains ammonium nitrate. Similarly, after the endothermic reaction takes place to produce a cold therapeutic member 102, the dental dressing 100 can be inserted into the user's oral cavity in the same manner described above.

In some embodiments of the dental dressing 100, the therapeutic member 102 is shaped substantially like a "U," and sized to engage one exposed tooth socket. In other embodiments, the therapeutic member 102 is shaped generally like a "U," but with tapered side members angularly extending from a cover portion. In yet other embodiments, the therapeutic member 102 has a "U-shaped" cross section, but is elongated to substantially engage a plurality of adjacent, exposed tooth sockets. In yet other embodiments, the therapeutic member 102 is shaped generally like an "H," with perpendicular or angled, tapered or non-tapered side members extending from a cover portion, to substantially engage substantially aligned maxillary 1101 and mandibular 1102 exposed tooth sockets. In other embodiments, the therapeutic member 102 has an "H-shaped" cross section, but is elongated to substantially engage a plurality of adjacent, substantially aligned maxillary and mandibular exposed tooth sockets.

In some embodiments, the dental dressing 100 includes a hydrogel insert 801 embedded substantially within the dressing matrix 101. In other embodiments, the dental dressing 100 includes an insert 801 substantially comprised of hydrogel, hydrocolloid, hydrofibre, and/or any combination thereof. One skilled in the art will recognize that other, moisture-releasing inserts can also be used without deviating from the scope or spirit of the general present inventive concept. These moisture-releasing inserts 801 are particularly applicable in instances where a dry socket forms after tooth extraction.

In some embodiments, the dental dressing 100 includes a topical agent insert 901. In some embodiments, the topical agent insert 901 is includes medications like eugenol, benzocaine, iodophorm, soluble aspirin, zinc oxide, or any combination thereof. In other embodiments, the topical agent insert 901 includes tannin. In some embodiments, the topical agent insert 901 is a tea bag. One skilled in the art will recognize that the present general inventive concept is not limited to the use of the specific substances described herein, but can also encompass other, topical agents that can be included in the insert 901 for topical application to an exposed tooth socket.

Numerous variations, modifications, and additional embodiments are possible, and accordingly, all such variations, modifications, and embodiments are to be regarded as being within the spirit and scope of the present general inventive concept. For example, regardless of the content of any portion of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated.

While the present general inventive concept has been illustrated by description of several example embodiments, it is not the intention of the applicant to restrict or in any way limit the scope of the inventive concept to such descriptions and illustrations. Instead, the descriptions, drawings, and claims herein are to be regarded as illustrative in nature, and not as restrictive, and additional embodiments will readily appear to those skilled in the art upon reading the above description and drawings.

The invention claimed is:

1. A dental dressing to promote healing and relieve pain and swelling associated with exposed dental alveoli, said dressing comprising:
   a three-dimensional dressing matrix to absorb leaked fluid associated with one or more exposed alveoli; and
   a therapeutic member to provide substantially localized cold therapy to said one or more exposed alveoli, wherein said therapeutic member is embedded substantially within said three-dimensional dressing matrix and is shaped to substantially engage said one or more exposed alveoli while fitting substantially between contiguous teeth, wherein said therapeutic member is comprised of a socket cover portion and at least two arm members extending from said socket cover portion, wherein said socket cover portion and said at least two arm members are contained within said three-dimensional dressing matrix, and further wherein said therapeutic member comprises a non-migrating gel contained within a membrane;
   whereby at least part of said dressing matrix substantially conforms to said one or more exposed alveoli, thereby engaging said therapeutic member with said one or more exposed alveoli.

2. The dental dressing of claim 1, further comprising:
a topical agent insert embedded substantially within said dressing matrix, substantially adjacent to said therapeutic member.

3. The dental dressing of claim 2, wherein said topical agent insert includes tannin.

4. The dental dressing of claim 2, wherein said topical agent insert includes at least one substance selected from a group consisting of eugenol, benzocaine, iodophorm, soluble aspirin, and zinc oxide.

5. The dental dressing of claim 1, further comprising:
a moisture-releasing insert, said insert embedded substantially within said dressing matrix, substantially adjacent to said therapeutic member.

6. The dental dressing of claim 5, wherein said moisture-releasing insert includes at least one substance selected from a group consisting of hydrogel, hydrocolloid, and hydrofibre.

7. The dental dressing of claim 1, wherein said dressing matrix is formed of at least one material selected from a group consisting of gauze, tulle, and cotton.

8. The dental dressing of claim 1, wherein said dressing matrix includes at least one substance selected from a group consisting of hydrogel, alginate, hydrofibre, collagen, and chitosan.

9. The dental dressing of claim 1, wherein said therapeutic member is substantially comprised of ammonium nitrate and water substantially contained within a polymer-based housing member.

10. The dental dressing of claim 1, wherein said therapeutic member is substantially comprised of rubbing alcohol and water substantially contained within a polymer-based housing member.

11. The dental dressing of claim 1, wherein said therapeutic member includes a substantially U-shaped cross section and is elongated to engage a plurality of adjacent, exposed alveoli.

12. The dental dressing of claim 1, wherein said therapeutic member is substantially H-shaped so as to engage substantially aligned maxillary and mandibular exposed alveoli.

13. The dental dressing of claim 1, wherein said therapeutic member includes a substantially H-shaped cross section and is elongated to engage a plurality of adjacent, exposed maxillary and mandibular alveoli.

14. The dental dressing of claim 1, wherein said therapeutic member is comprised of a socket cover portion and at least two tapered arm members angularly extending from said cover portion.

15. The dental dressing of claim 1, wherein said therapeutic member has substantially U-shaped cross section so as to engage at least one said exposed alveoli.

\* \* \* \* \*